(12) United States Patent
Maack et al.

(10) Patent No.: US 10,789,674 B2
(45) Date of Patent: Sep. 29, 2020

(54) SPACIAL FLICKER REMOVAL AT LOW FRAME RATES IN FLUOROSCOPY

(71) Applicant: KONINKLIJKE PHILIPS N.V., Eindhoven (NL)

(72) Inventors: Hanns-Ingo Maack, Norderstedt (DE); Tobias Reusch, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 211 days.

(21) Appl. No.: 15/760,637

(22) PCT Filed: Sep. 21, 2016

(86) PCT No.: PCT/EP2016/072379
§ 371 (c)(1),
(2) Date: Mar. 16, 2018

(87) PCT Pub. No.: WO2017/050802
PCT Pub. Date: Mar. 30, 2017

(65) Prior Publication Data
US 2018/0253822 A1 Sep. 6, 2018

(30) Foreign Application Priority Data

Sep. 25, 2015 (EP) ..................................... 15186918

(51) Int. Cl.
*G06K 9/00* (2006.01)
*G06T 3/40* (2006.01)
(Continued)

(52) U.S. Cl.
CPC .............. *G06T 3/40* (2013.01); *A61B 6/4441* (2013.01); *H04N 5/32* (2013.01); *G06T 2207/10121* (2013.01)

(58) Field of Classification Search
None
See application file for complete search history.

(56) References Cited

U.S. PATENT DOCUMENTS 5,224,141 A 6/1993 Yassa
5,400,383 A 3/1995 Yassa
(Continued)

OTHER PUBLICATIONS

Didyk P. et al., "A Question of Time: Importance and Possibilities of High Refresh-Rtes", Jan. 1, 2009 (Jan. 1, 2009), Visual Computing Research Conference 2009, pp. 1-3, XP055257178, URL : http .-//people.mpi -inf. mpg.de/"pdidyk/question_of_time.pdf.
(Continued)

*Primary Examiner* — Atiba O Fitzpatrick
(74) *Attorney, Agent, or Firm* — Larry Liberchuk (57) ABSTRACT

An image processing module and related method. The module (IP) comprises—one or more input interfaces (IN) configured for receiving i) a first input image (II) acquired of an object by an imaging apparatus (IM) at a first geometrical configuration of the X-ray imaging apparatus and ii) a specification of a change from said first geometrical configuration to a second geometrical configuration of the imaging apparatus. An upsampler component (US) of the module (IP) computes a new image (I$^+$) of the object (OB) by applying a geometrical transformation to said first input image. The geometrical transformation corresponds to said change in geometrical configuration of the imaging apparatus.

9 Claims, 4 Drawing Sheets

(51) Int. Cl.
*A61B 6/00* (2006.01)
*H04N 5/32* (2006.01)

(56) References Cited

U.S. PATENT DOCUMENTS

| | | | |
|---|---|---|---|
| 6,418,186 B1* | 7/2002 | Kawai | A61B 6/032 378/15 |
| 6,690,386 B2* | 2/2004 | Edelson | G06F 19/321 345/634 |
| 8,243,194 B2 | 8/2012 | Ozdemir | |
| 2007/0140427 A1 | 6/2007 | Jensen | |
| 2010/0128955 A1 | 5/2010 | Walimbe | |
| 2016/0063740 A1* | 3/2016 | Sakimoto | G06T 11/005 382/131 |
| 2017/0018054 A1* | 1/2017 | Holzer | G06K 9/00664 |
| 2017/0018055 A1* | 1/2017 | Holzer | H04N 13/111 |
| 2017/0018056 A1* | 1/2017 | Holzer | G06K 9/00664 |

OTHER PUBLICATIONS

Idyk P. et al., "Perceptually-Motivated Real-Time Temporal Upsampling of 3D Content for High-Refresh-Rate Displays", Computer Graphics Forum, vol. 29, No. 2, May 1, 2010 (May 1, 2010), pp. 713-722, XP05525717.

Yasuyuki Matsushita et al: "Full-Frame Video Stabilization with Motion Inpainting", IEEE Transactions on Pattern Analysis and Machine Intelligence, IEEE, USA, vol. 28, No. 7, Jul. 1, 2006 (Jul. 1, 2006), pp. 1150-1163, XP001523476.

Koenig T. R. et al., "Skin Injuries from Fluoroscopically Guided Procedures: Part 2, Review of 73 Cases and Recommendations for Minimizing Dose Delivered to Patient", American Journal of Roentgenology, vol. 177, Jan. 1, 2001, pp. 13-20, XP55519761.

Steffenino G et al., "Staff Dose Reduction During Coronary Angiography Using Low Framing Speed", British Journal of Radiology, British Institute of Radiology, London, GB, vol. 69, No. 825, Jan. 1, 1996 (Jan. 1, 1996 ), pp. 860-864, XP009509000.

\* cited by examiner

SPACIAL FLICKER REMOVAL AT LOW FRAME RATES IN FLUOROSCOPY

FIELD OF THE INVENTION

The invention relates to an image processing module, to an image processing method, to an imaging arrangement, to a computer program element, and to a computer readable medium.

BACKGROUND OF THE INVENTION

The use of interventional X-ray procedures is associated with significant risks caused by the applied ionizing radiation. Short term radiation injury due to high peak skin X-ray dose and long term injuries such as cancer are well known issues. There are therefore ongoing efforts in the medical profession to find ways to reduce the radiation dose as much as possible.

For the case of interventional or diagnostic procedures, which rely on dynamic image sequences (i.e., fluoroscopy or angiography), there is the option to reduce the applied X-ray dose by lowering an acquisition frame rate and hence the number of individual exposures. Low frame rates of 8 fps (frames per second) and below are routinely used in clinical practice.

However, this approach may compromise the quality of the dynamic image sequence as motions occurring during the imaging may lead to an unnatural viewing experience with stop-motion character.

To enable a smoother viewing experience, image processing schemes have been proposed in the past where additional frames are interpolated from earlier and later frames. But these schemes have been found at times to be too laggy.

SUMMARY OF THE INVENTION

There may therefore be a need for alternative forms of image processing for dynamic imaging.

The object of the present invention is solved by the subject matter of the independent claims where further embodiments are incorporated in the dependent claims. It should be noted that the following described aspect of the invention equally apply to the image processing method, to the imaging arrangement, to the computer program element, and to the computer readable medium.

According to a first aspect of the invention there is provided an image processing module, comprising:
  one or more input interfaces configured for receiving i) a first input image acquired of an object by an imaging apparatus (IM) at a first geometrical configuration of the imaging apparatus and ii) a specification of a change from said first geometrical configuration to a second geometrical configuration of the imaging apparatus; and
  an up-sampler configured to compute a new image (also referred to hereinafter as a "filler frame") of the object by applying at least one geometrical transformation to said first input image, wherein said geometrical transformation corresponds to said change in geometrical configuration of the imaging apparatus.

According to one embodiment of the image processing module according to the present invention, the image processing comprises a visualizer configured to effect on a display unit, a sequential visualization of, first, said first input image, and then said filler frame.

According to another embodiment of the image processing module according to the present invention, the visualizer is operative to effect, after said sequential visualization, a visualization of a second input image acquired at said second geometrical configuration of the imaging apparatus.

The image processing module according to the present invention is capable of operating at real time, that is, whilst the change if effected. The insertion of the computed fillers into the sequence of acquired images (in particular, the first input image and the second input image) affords generating a motion picture with smooth transitions thus compensating for the stop-motion effect. The one or more compute filler images are approximations of the second, subsequent image to be acquired. Hence, displaying in a time sequence, the first and image and then the filler frames will smoothen the visual experience.

According to another embodiment of the image processing module according to the present invention, the specification of the change from the first to the second geometrical configuration is supplied in the form of hardware measurement data in relation to the imagining apparatus. These hardware measurements may be picked up at one or more manually or automatic actuators that effected or are to effect the specified change of the geometrical configuration of the imaging apparatus. This allows computing the filler frames as realistic approximations of the second image with high responsiveness thus low latency.

According to another embodiment of the image processing module according to the present invention, a plurality of filler frames is computed by said up-sampler, one for each of a plurality of received specifications of changes in geometrical configuration of the imaging apparatus, the number of said plurality of filler frames being dependent on a refresh rate of said visualizer. This allows further improving the visual impression and the display module can be used for more efficiently. Rather than repeatedly displaying the latest available image pending receipt of the second frame, the filler images are displayed in sequence until the second image is received.

According to another embodiment of the image processing module according to the present invention the imaging apparatus is an X-ray imaging apparatus, and the geometrical configuration of the imaging apparatus includes any one or a combination of: (i) a position and/or orientation of a support on which the object to be imaged resides during an image acquisition; (ii) a position and/or orientation of an X-ray source of said X-ray imaging apparatus; (iii) a position and/or orientation of a detector of said imaging apparatus, and (iv) a position and/or orientation of a collimator component.

According to another embodiment of the image processing module according to the present invention, the at least one filler frame comprises image information retained from the first input image and placeholder data that replaces image information from the first input image lost due to the application of the geometrical transformation. The placeholder data can be used for instance to alert the user (the viewer that is) visually to the fact that "artificial" information has been included in the filler image that is being displayed. Alternatively, it may be desirable to configure the placeholder data so as to "hide" the loss of information to not distract the viewer.

According to another embodiment of the image processing module according to the present invention, the geometrical transformation includes moving, relative to a reference coordinate system, said first input image by an amount that corresponds to said change in geometrical configuration of the imaging apparatus. This further helps achieve smoothen the visual experience for the user.

In other words, the image processing module according to the present invention allows creating an up-sampled image sequence from the earlier image and knowledge about the change of the geometrical configuration of the imaging apparatus. Knowledge of the later, follow up, acquisition image is not required thus increasing responsiveness of the proposed module as compared to image-based interpolation methods that rely on processing pairs of acquired image. In the proposed method, there is no interpolation from image pairs, but the filler frames are extrapolated from, preferably, a single, available acquired image I1 and the specified imaging geometry change. Preferably, the specification of change of the geometrical configuration is based on said hardware measurements acquired in relation to the imager supplying the first input image. Preferably the specification is supplied in quasi-real time. The specification may be based on information obtained from motion encoders or instead of or in addition to readings from mechanical/electrical/optical measuring techniques. The readings for the specification of the change of geometrical configuration may be supplied by suitable pick-up circuitry that interfaces with the one or more actuators that effect or are about to effect the change. Position and/or motion sensors arranged external to the imaging apparatus are also envisaged instead of or in addition to readings supplied internally by the respective actuator and/or motion encoders.

The image processing module according to the present invention can be used with benefit in several ways. For instance, the proposed imaging module allows for a smoother viewing experience without changing the acquisition frame rate f of the imaging apparatus. Conversely, the acquisition frame rate can be lowered to $f_2 < f$. Normally then, the perceived smoothness, when displaying such a sequence, will thus be inferior compared to a sequence recorded at the higher frame rate f But with the proposed image processing module, the low rate sequence can be up-sampled to secure a viewing experience at a smoothness level similar to that afforded by the image sequence recorded at the higher rate f. This allows effectively reducing X-ray dosage.

According to a further aspect of the present invention, there is provided a method of image processing, comprising the steps of:
   receiving i) a first input image acquired of an object by an imaging apparatus at a first geometrical configuration of the imaging apparatus and ii) a specification of a change from of said first geometrical configuration to a second geometrical configuration of the imaging apparatus; and
   computing a filler frame by applying at least one transformation to said input image, wherein said transformation corresponds to said change of said geometric configuration of the imaging apparatus.

According to one embodiment of the method of image processing according to the invention, this further comprises the step of displaying on a display unit, in sequence, first, said first input image, and then said filler frame.

According to another aspect of the invention, there is provided an imaging arrangement comprising:
   a module of according to any one of the above mentioned embodiments; and
   the imaging apparatus for supplying at least one input image for processing by said module.

According to one embodiment of the imaging arrangement according to the invention, this further comprises a display unit for displaying said input image and image data produced by said module.

According to another aspect of the invention, there is provided a computer program element for controlling a module according to any one of the above mentioned embodiments, which computer program element, when being executed by a processing unit is adapted to perform the method steps of any one of the above mentioned embodiments of the method of image processing.

According to another aspect of the invention, there is provided a computer readable medium having stored thereon the program element mentioned above.

The main field of application for the image processing module, the method for image processing, the imaging arrangement the computer program element and the computer readable medium envisaged herein is for X-ray imaging, in particular fluoroscopy or angiography. More specifically, the imaging apparatus may be an X-ray imaging apparatus. Such X-ray imaging apparatus may be arranged for fluoroscopy, angiography, diagnostic X-ray and/or interventional X-ray. However, other applications for the proposed module are not excluded herein. The proposed image processing module may also be used more generally as an image stabiliser component in other imaging modalities.

In this text, "geometrical configuration of the imaging apparatus" refers to any given mutual configuration in 3D space of the X-ray source and/or the detector relative to the region of interest to be imaged system. It further includes manipulations of the X-ray beam such as by collimation, etc., and that affect the field of view. The geometrical configuration of the imaging apparatus will be referred to hereinafter as "imaging geometry" for short.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
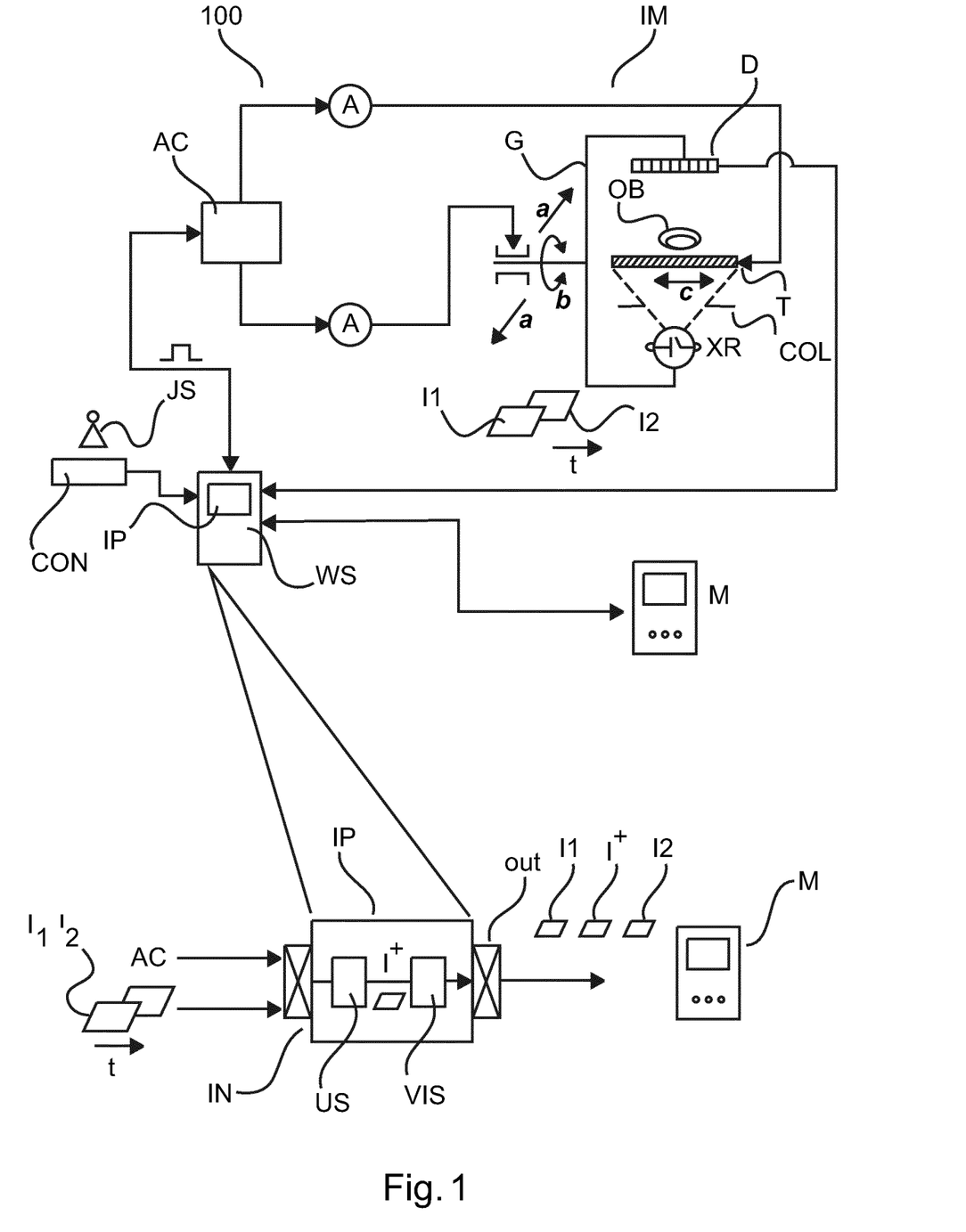
FIG. 1 shows an imaging arrangement.

With reference to FIG. 1, there is shown an imaging arrangement 100 comprising an imaging apparatus IM.

In one embodiment, the imaging apparatus comprises an X-ray source XR and an X-ray radiation sensitive detector D. More specific embodiments include fluoroscopic imaging equipment or angiographic imaging equipment. Although the main focus is on X-ray imaging and the invention will be explained in this context, other, in particular non-X-ray imaging equipment is not excluded herein.

The X-ray source XR and/or the detector D is movable relative to an examination region envisaged between the X-ray source XR and/or the detector D. The examination region is suitably spaced to receive an object OB to be imaged. In one embodiment, the imaging apparatus includes a support T, such an examination table, on which the object (or a part thereof) resides in the examination region during imaging.

In one embodiment, the X-ray source and/or detector D are arranged on a gantry. The gantry is rotatable and/or translatable around or relative to the examination region thus enabling motion of the source XR and/or the detector D relative to the object, or at least relative to a region of interest (ROI) thereof, in the examination region.

In one embodiment, the X-ray imaging apparatus further includes collimation equipment (COL) to restrict the imager IM's field of view. One or more collimator blades formed from a high density material are positioned into the X-ray beam to block out unwanted parts of the radiation for a given imaging task. Positioning and/or orientation of the collimator blades are achieved automatically (by one or more actuators) or manually.

The object OB to be imaged can be animate or inanimate. In medical applications for interventional or diagnostic purposes as mainly envisaged, the animate "object" is an animal or human patient or a relevant part thereof.

The imaging apparatus IM allows acquiring one or more projection images of the ROI. The X-ray projection imagery encodes information on the internal configuration or constitution of the object. The, preferably 2D (two-dimensional), imagery acquired by the X-ray imaging apparatus can be displayed on a monitor M.

In operation, the X-ray source XR emits X-radiation which is projected across the region of interest in the examination region. The projected radiation interacts with matter in ROI. This interaction results in information on the internal constitution being modulated onto the radiation and the so modulated radiation is then incident on the detector D. The detector comprises a plurality of radiation sensitive elements (pixels) which produce electric signals in response to the incident radiation. The electric signals are converted by suitable DAS circuitry (not shown) into digital raw data. The raw data is then passed through one or more stages of signal processing circuitry to extract the modulated information to produce one or more digital images encoding the desired spatial distribution of a quantity of interest such as absorption (as in traditional radiography) or refraction (phase contrast imaging) or small angle scattering (dark field). To be able to extract the information for the later to cases, the imaging apparatus may further include suitable interferometric equipment with which the radiation interacts additionally before being incident on the detector.

In order to be able to increase an effective field of view of the imager IM or to acquire medically relevant images for given imaging task, an imaging geometry of the imager IM can be changed. The imaging geometry defines the mutual configuration in 3D space of the X-ray source and/or the detector relative to the region of interest to be imaged. That is, imagery from different projection directions can be acquired thanks to the adjustable imaging geometry. In general, the imaging geometry is defined by position and/or orientation of system components, or more specially X-ray optical components, that have an effect on how the X-ray radiation interacts spatially with the detector. The imaging geometry definition also includes orientation and or position of the collimator blades (if any) relative to the X-ray beam.

The manner in which the change of imaging geometry can be effected will depend on the particular construction of the imaging apparatus. For instance, in the embodiment where the X-ray imager IM has the rotatable gantry G, such as in imagers of the C-arm type, the change in imaging geometry can be achieved by rotating and/or translating the C-arm relative to the object OB to be imaged. These degrees of freedom are indicated in FIG. 1 by arrows a, b. In this way, at least the position of the X-ray source relative to the ROI (to be imaged) can be changed by moving the X-ray source from one position to another by rotating and or translating the C-arm G. Other embodiments envisage instead a fixed detector whereas it is only the X-ray source that is moveable. Another way to change the imaging geometry is by moving the examination table with the object thereon to adjust the effective field of view of the imager. As schematically indicated by arrow c, the table T, if any, may be translatable along a first axis relative to an (at least instantaneous) optical axis of the imaging apparatus IM or the table may independently translatable in two spatial dimensions, that is, in addition to a translation along a first axis, the table is translatable along a second axis across the first axis.

The change in imaging geometry is effected by controlling suitable (preferably automatic) actuators A such as stepper motors or servo motors, etc. associated with the respective machine part of the imaging apparatus IM. The respective machine part may be for instance the X-ray source, or the gantry (having the source XR mounted thereon) and/or the exam table T, etc. The one or more actuators A are controlled by actuator controller circuitry AC. The actuator control circuitry AC responds to control signals issued from an operator console CON. In one embodiment the console CON includes a user input device such as a joy-stick arrangement JS which allows a user to precisely adjust the imaging geometry. For instance, the joy stick JS allows the user to rotate or translate the X-ray source and/or the detector and/or to translate or incline the examination table T and so on. The user input device allows the user to issue suitable control commands which are forwarded through a wired or wireless communication infrastructure to the actuator control circuitry AC. The control commands are then translated into by the actuator control circuitry AC into lower level machine signals to then activate the one or more actuators A to bring about the desired change in imaging geometry. For instance, the control commands may specify a rotation angle by which the C-arm is to be rotated or they may specify the distance (in centimeters or millimeters or in any other suitable unit of length) by which the examination table T is to be translated.

Once the imager has assumed the desired imaging geometry, a sequence of two or more X-ray images I1 and I2 are acquired in one or more imaging runs. In each imaging run a burst of X-ray exposures are issued to acquire one sequence of X-ray images I1,I2 at a certain frame rate, for instance 5-10 fps. In between two imaging runs, a change of imaging geometry may be called for and a new sequence of imagery is then acquired once the new geometry has been assumed by the X-ray imaging apparatus. It may also be the case that the imaging geometry is being changed whilst the images are acquired in a run.

The sequence of projection images I1,I2 are displayable in temporal sequence on the display unit M thereby creating essentially a motion picture that allows the user to monitor the internal dynamics of the object OB and/or the position of a (medical) device that resides in the object OB. For instance, in cardiac interventions under fluoroscopic guidance, to name but one exemplary field of application envisaged herein, a catheter is advanced through the patient's cardiovasculature to a lesioned site (a stricture for instance). The motion picture allows one to track the catheter position throughout its course. Also, physiological activities can be monitored to assess performance. E.g., in absorption imagery based angiography, cardiac activity or perfusion of a part of the cardio-vasculature can be monitored by displaying the motion picture based and the sequence of images acquired whilst a quantity of contrast agent resides at the region of interest to confer the required radio-opacity.

The visual appearance or quality on the monitor of the motion picture may occasionally comprise non-smooth transitions which are perceived as jerky or flickering motions of image structures between subsequently acquired images I1 and I2. This may be caused by the change of imaging geometry either during a given imaging run or between two consecutive imaging runs.

In order to ensure a visually smooth display of the imaging sequence, the proposed imaging arrangement 100 comprises an image processor or module IP that operates to compensate for image flicker by producing one or more filler frames that together encode motion that occurred during imaging geometry changes between two different image acquisitions. The filler frames are produced by applying one or more transformation to the earlier image. The transformation captures the motion caused by the imaging geometry change. The image processor may run as a software module on a workstation WS associated with the imaging apparatus IM. Alternatively, some or all components of the image processor IP may be arranged in hardware such as a suitably programmed FPGA (field-programmable-gate-array) or as a hardwired Integrated circuit (IC) chip.

The lower part of FIG. 1 shows a block diagram close-up of functional parts of the image processor IP. The image processor IP comprises: an input port IN and an output port OUT, an up-sampler US and a visualizer VIS.

Very broadly, the image processor IP computes one or more filler frames I+ for inclusion between two consecutive image images I1 and I2 acquired by the imaging apparatus IM. The filler frames are computed based on an earlier acquired frame i, referenced herein as I1, and preferably real time information acquired from the imaging apparatus about the imaging geometry change that occurred since the X-ray image I1 was acquired or that is still to occur. The information specifies the change from a first imaging geometry (at which the earlier image I1 was acquired) to a second imaging geometry at which a later image, I2, was or is to be acquired. Both, the earlier image I1 and the specification of the imaging geometry change are received at one or more input ports IN. Based on this input, the up-sampler US computes a single or, preferably, a plurality of filler frames $I^+$ from the earlier image I1 for insertion as a sequence between the acquired frames I1,I2 to so form an up-sampled imagery sequence. The earlier image I1 and the one or more filler frames are then displayed in sequence by operation of visualizer VIZ which interacts with video software that drives the display generation at the monitor M. More specifically, the sequential displaying effected by the visualizer VIS starts with the earlier frame I1, then the one or more filler frames are the displayed in sequence on the monitor M. Eventually it is then the later frame I2 that is displayed after the last filler frame I+ has been displayed. The display sequence, as seen by the human observer on monitor M, segues smoothly from the earlier image I1 via the filler frames I+ into the later frame I2. The filler frames are essentially extrapolated from the earlier image and from the knowledge about the motion involved or to be involved in the change from the first to the second imaging geometry. Knowledge of the later X-ray image I2 itself is not required for the extrapolation of the filler frames. This allows reducing a lag time which is prevalent in previous approaches that rely on interpolation between two actually acquired images. Said differently, in the approach proposed herein, processor IP is "informed" beforehand about the motion incurred by the imaging geometry change. The filler frames can then be computed even before the second imaging geometry is actually assumed or before the later X-ray image I2 is actually acquired. The filler frames are computed to together encode this motion such that, when these filler frames are displayed in a cine sequence, image flicker is eliminated or at least reduced when, eventually, the later image I2 is displayed. The filler frames are gradual transitions or "morphings" from the earlier image I1 to an estimate how the later image I2 may look like. In particular the last filler frame in the sequence is expected to be a good approximation of the next image I2. And by displaying in sequence the earlier image I1 and the filler frames I+, this transition between the earlier and later image can be softened to thereby achieve the flicker reduction.

This real time specification of the change in imaging geometry can be acquired by general electrical optical sensors arranged at or in relation to the actuators. The change of imaging geometry information can also be obtained directly by interfacing with the actuators or can also be inferred by intercepting the control commands which are issued by the user input means for instance.

The up-sampler US computes the filler frames by applying one or more image transformations to the earlier image I1 to achieve the flicker reduction effect. The transformation encodes at least in approximation, the specified imaging geometry change in terms of a suitable functional expression such as one or more vectors or matrices. The transformation is computed from the change of image geometry readings. In one embodiment the transformation is a shift operation. The shift transformation is applied to shift the earlier X-ray image I1 by an amount that corresponds or approximates a displacement used or to be used in the imaging geometry change. More generally, the transformation is a rigid or a non-rigid transformation or a transformation that allows accounting for magnification effects caused within the image signal path of the X-ray imaging apparatus.

In general, not just a single, but a plurality of such filler frames are computed by decomposing a motion as per the imaging geometry change into smaller components, the number of which corresponds to the up-sampling factor to be used which is either pre-set or can be adjusted by the user. The one or more filler frames I+ are then displayed in sequence after display of the earlier frame I1 until eventually the second image frame I2 is displayed. Respective shift transformations, applied one-by-one to the earlier frame I1 to compute the one or more filler frames I+, are taken relative to a reference coordinate system. For instance, in one embodiment the reference coordinate system is specified by the edges of the earlier image I1 when displayed on the monitor M.

Figure 2:
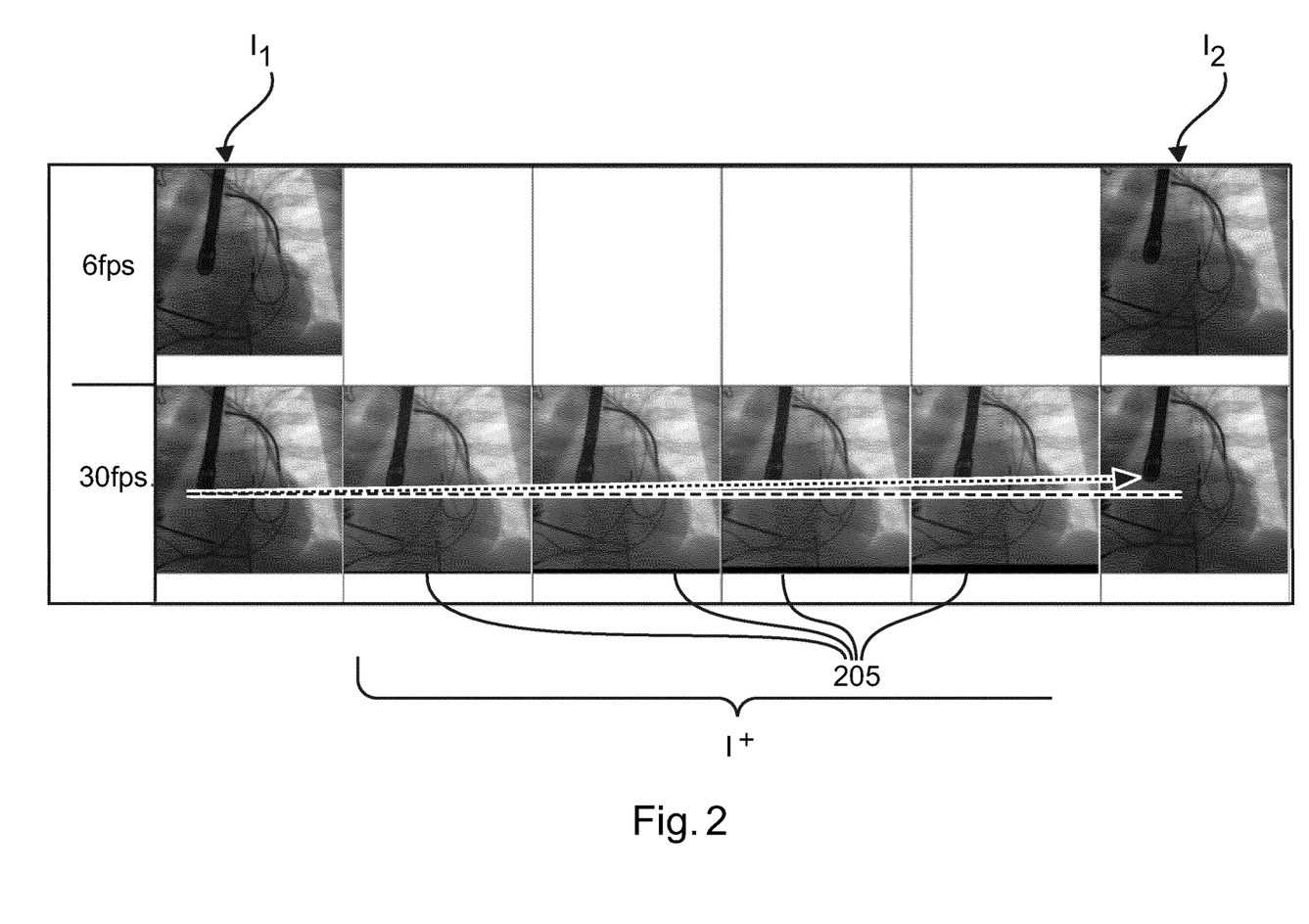
FIG. 2 shows an up-sampled image sequence according to a first embodiment.

FIG. 2 is an illustration of the operation of the proposed image processing apparatus IP. The upper row shows the two images I1 and I2 acquired at a given frame rate, for instance 6 fps. The acquisition frame rate is usually in the region of 3 fps-15 fps. The lower row shows four filler images I+ inserted between the two frames I1 and I2 and displayed in that sequence. The frame rate has been thus increased five-fold from 6 fps to 30 fps. The dashed line shows a reference base line and the arrow illustrates the effect of the pixel transformations are applied to the earlier image I1 as simple shifts, in this example in a positive direction along the vertical y axis of the image screen M. In other words, the filler images are, in this case, shifted copies of the earlier X-ray image I1. Accumulation of the individual shifts across the individual filler frames I+ are shown by the inclination of the dotted arrow. Because of the shifts, some image information is lost which presents as undefined or void regions 205. The void regions 205 can be rendered for instance by filling the void pixel positions with black (as in the Figure) or by another suitable color. A deliberately conspicuous rendering, relative to the surrounding reals image information, of said voids 205 may be chosen to clearly indicate to the viewer that the void regions 205 represent mocked information to which no interpretative (diagnostic or otherwise) value should be attached.

Figure 3:
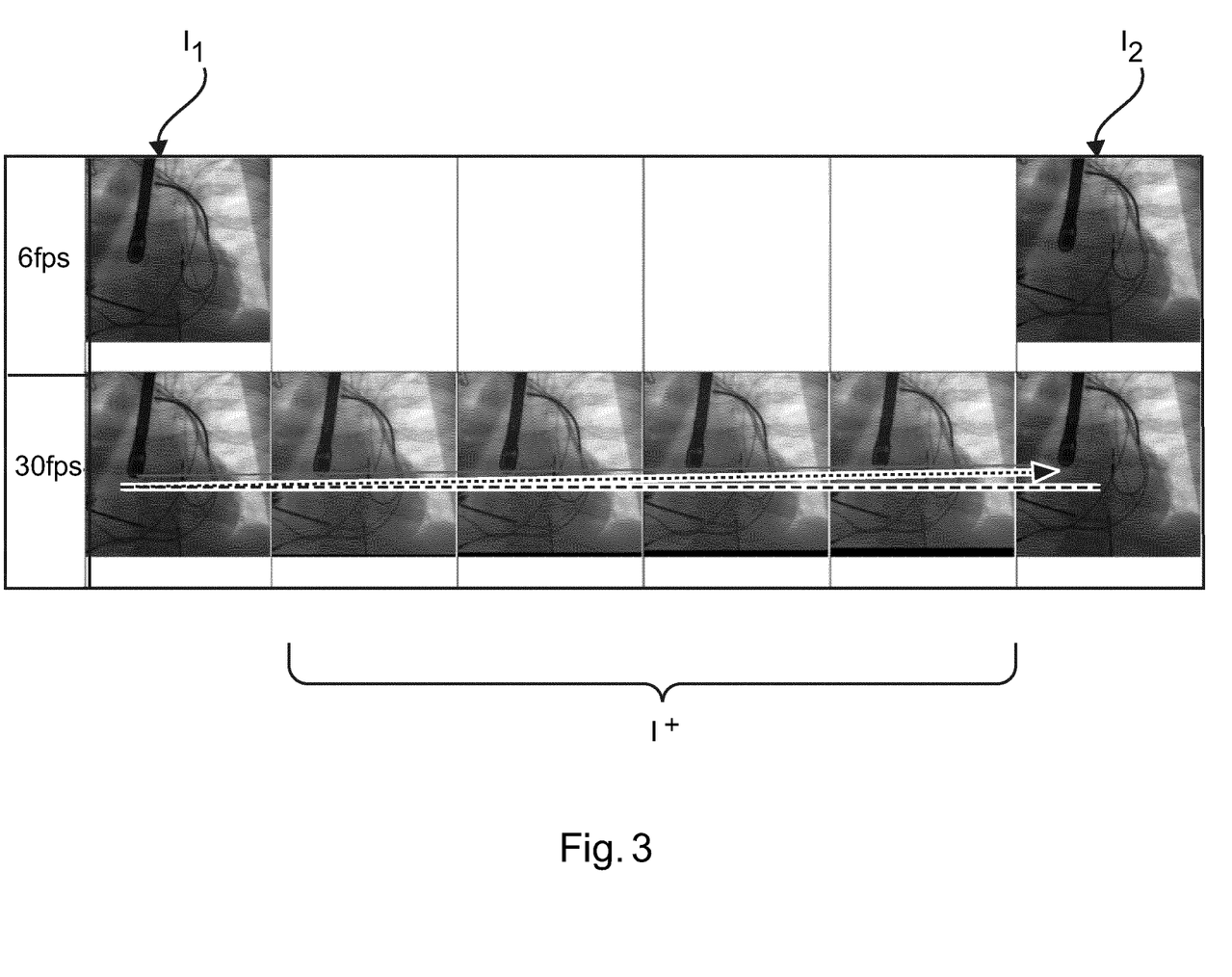
FIG. 3 shows an up-sampled image sequence according to a second embodiment.

In other, alternative, embodiments the void regions 205 can be filled by interpolation from neighboring pixel information so as to effectively hide from the viewer the loss of image information. In particular, the void pixel positions can be filled with the last pixel line in the direction of movement (i.e. the last line of the known image I1 is repeated several times). FIG. 3 is an illustration of this. This embodiment helps avoid the sort of visual distraction on the viewer that may arise if the gap regions were filled in a conspicuous manner as per the earlier mentioned embodiment.

Preferably, the number of filler frames to be inserted between the two consecutive X-ray images I1,I2 (supplied by the imager), is adjusted to a ratio between the frame rate of the X-ray imager and the refresh rate of the display unit M. The refresh rate (usually about 60 fps or higher) defines the minimum time period required to display two consecutive images. The frame rate of the X-ray imager is usually significantly lower than the refresh rate of the monitor M. The image transformation may then be sub-divided into parts, which are then cumulatively applied in steps, part by part, to the earlier X-ray image to compute the required number N of filler frames, akin to the illustration in FIGS. 2,3 above. This number N, which determines the up-sampling factor N+1, can be adjusted to the ratio between the monitor refresh rate and the frame rate of the X-ray imager. By way of a non-limiting numerical example, given an X-ray image acquisition rate of 5 fps and a monitor refresh rate of 60 fps, 60/5−1=11 filler frames are computed. If the received geometry change specification calls for a translation of patient bed by 5 cm (again, this is purely exemplary and not limiting) between two consecutive images I1,I2, this distance is sub-divided into partial shift-vectors of 5/12 cms. These partial shifts (which together combine to the total shift of 5 cm) are then cumulatively applied as per $5/12*i$ (i=1 . . . 12) to the earlier image I1 to yield the filler frames $I_i^+$, for each i.

A consequence of using the proposed filler frames is an effective "image refresh rate" on the screen M significantly higher than the nominal X-ray exposure rate, in particular when a plurality of filler images are computed as above and inserted between consecutive X-ray images I1,I2.

In one embodiment, it is envisaged for the up-sampling factor to be adjustable based on user input. The user specifies the refresh rate and/or acquisition rate. This input is then forwarded to the up-sampler US where the up-sampling factor for computing the filler frames is the adjusted based on the ratio as explained above. Alternatively, the up-sampling factor is adjusted automatically.

Figure 4:
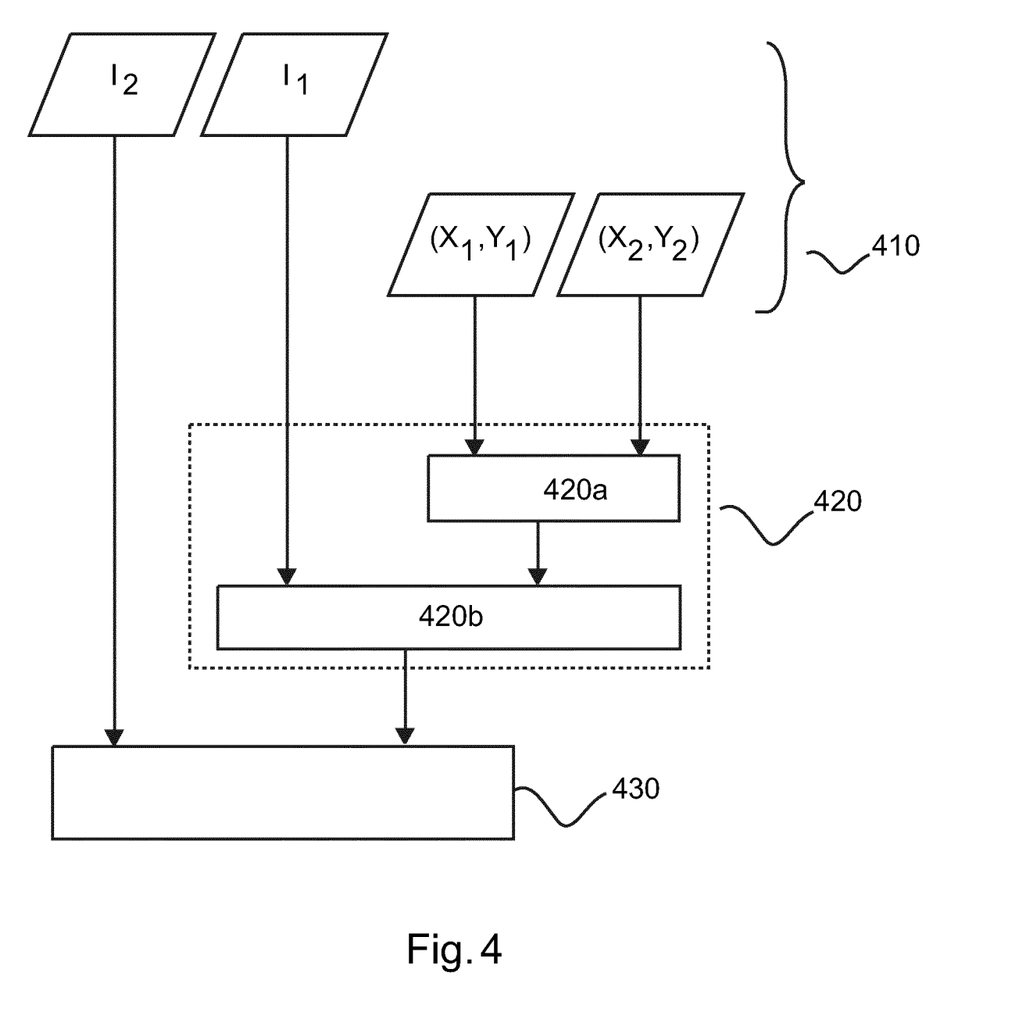
FIG. 4 shows a flow chart of an image processing method.

Reference is now made to flow chart in FIG. 4 to explain the image processing method as implemented by the image processor IP in more detail. It will be understood herein that the flow chart and the corresponding explanation is not necessarily tied to the architecture shown in FIG. 1, but can also be read by those skilled in the art as stand-alone instructions.

At step S410, a first input image I1 acquired by the image apparatus is received. The frame I1 is assumed to have been acquired at a first imaging geometry by the imaging apparatus. In addition to the input image frame I1, but not necessarily concurrently with said input image I1, a specification is received that specifies a change from a first to a second imaging geometry. The specification is schematically indicted in FIG. 4 in coordinates "$(X_1,Y_1)$" (indicating a "first" imaging geometry) and "$(X_2,Y_2)$" (indicating a "second" imaging geometry), with the understanding that other formats, in particular in angular specifications, are not excluded herein.

The specification for the change in imaging geometry can be embodied for instance by a control command, or a real time reading or measurements as supplied by one or more motion encoders associated with one or more actuators involved in bringing about the change in imaging geometry. Signal used to drive the actuators can also be used (after appropriate conversions) as an imaging geometry specification. For instance, in embodiment the patient bed is translated by a certain amount (specifiable in cm or mm or other suitable unit), and this amount in included in said imaging geometry change specification. The translation amount can be obtained directly from a motion encoder associated with the actuator A that brings about the translation. Preferably, in order to promote quasi-real-time responsiveness, the specification is obtained as velocity readings (speed and direction) to be applied to a relevant machine part. In other embodiments the reading is post-factum and specifies the displacement already experienced. In this later case, there will a slight lag in response time which, however, has been found in general to not appreciably disturb the real-time impression as experienced by the viewer.

Other examples or geometry change specifications are the rotation in degree by the X-ray source around the region of interest. More generally, the specification may also include inclination data to in respect of respective of changes of orientation around one more axes of the X-ray tube, detector plane or patient bed.

The specification may specify a combination of motions such as one or more translations, possibly along different axis and one or more rotations, etc. The specification is preferably supplied from the imaging apparatus via its (automatic) actuators.

If the imaging apparatus is not fully motorized, it may include manually operable actuators such as levers or other gearing mechanism. For instance, some patient beds are translated by the user operating one or more handwheels coupled to the bed T via suitable gearing mechanisms. In these cases, suitable internal sensors may be installed at the manual actuators to translate motions such as rotations/translations with the actuator mechanism into digital readings that correspond directly or indirectly (after suitable conversion) to the effected patient motion. Alternatively, rather than mounting internal sensor equipment at the relevant actuators sensors external to the imaging apparatus may be used instead. For example a system of one or more photo-electric sensors may be installed on the outside of the imaging equipment to measure the number of time a certain manually operable actuator (such as a hand or thumbwheel) is turned and these counts are then convertible into patient motion distances. Of course, using photoelectric sensors in this manner is also suitable when measuring imaging geometry changes caused by automatic actuators. In general, where the actuators are automatic or manual, any measurement technique optical, electrical or mechanical to capture the change of imaging geometry specification is envisaged herein.

Once the imaging geometry change specification has been measured, flow control passes on to step S420 where one or more filler images are then computed based on the specification of the change of geometry. The step 420 for computing the one or more filler frames I+ comprises two sub-steps.

In one sub-step 420a, an image transformation is computed based on the specified imaging geometry change. For instance in one embodiment a translation or shift vector is extracted from the received specification of the imaging geometry change. In some instance, the motion (shift and/or rotation) as recorded on the specification can be directly taken (after conversion into pixel information) to indicate the transformation. This has been found to be true in particular for effective displacements $\Delta x \leq 1$ cm, whether or not the underlying motion is linear. This affords a convenient form of motion linearization where effects caused by the underlying projective geometry can be neglected. In other cases, where the imaging geometry change involves translations in excess of 1 cm, one or more preprocessing stages, for instance for conversion operations, may be necessary to arrive at the effective motion components for definition of the required image transformation. In one embodiment, this preprocessing may include decomposing the motions/displacements as recorded in the specification into components by projection onto the image plane of the detector at the imaging geometry at which the first image frame I1 has been acquired. In some embodiments, the conversion may include taking the inverse of the actually specified displacement to account for possible mirror-effects caused by the imaging setup. In one embodiment, the conversion stage/operation also takes into account X-ray optical magnification incurred in the image signal path. For instance, in C-arm X-ray imaging, a translation of the patient through the iso-center may incur a magnification factor of 2. In other words, the real motion in the examination region is recorded in the image plane by the detector as a magnified or "virtual" motion twice that of the real motion. These magnification effects in relation to speed or distance may be known beforehand as a prior-data which can then be applied to adjust the geometry change specification by the appropriate amount. Otherwise, absent such a priori knowledge, the magnification factor may be obtained in a simple calibration measurement: merely two test images are acquired of a movable test object to compute the magnification factor from the known displacement or speed to which the test object is subjected to whilst the two (or more) test images are acquired.

As mentioned, setting up of the image transformation includes conversion into pixel dimensions. This operation is based on the pixel pitch of the detector. Assuming for example a table movement at a speed of v=4 cm/s and a frame rate of f=8 fps the movement between two consecutive acquisitions amounts to $\Delta x$=5 mm. Further assuming a pixel pitch of 154 µm this corresponds to a jump of 33 pixels. The transformation can thus be defined by a shift vector of 33 pixels in x direction.

At sub-step S420B the one or more transformations determined in step S420b are then applied to, preferably, the latest available image frame I1 supplied by the imaging apparatus. The transformation is applied pixel-wisely to the image frame I1 to thereby rotate or translate, in one embodiment only translate, said frame relative to a reference coordinate system. The reference coordinate system (shown in FIGS. 2,3 as the horizontal dashed line) may be defined for instance by the window portion on the screen M on which the first image I1 is to be displayed.

At step S430 the first input image and the one or more filler frames are then rendered for display on the screen. The first image I1 is displayed first and then the filler(s) frames is/are sequentially displayed. Finally, it is then the second image I2 as supplied by the imaging apparatus that is displayed on the monitor M.

The method allows computing an up-sampled sequence from the original image I1 as supplied by the imager and the one or more transformations computed from the change of imaging geometry specification. The filler frames are computed without knowledge of the follow-up image I2. The upsampled sequence presents to the viewer a more realistic visual experience with smooth transitions between the sequentially displayed image information. In particular, flicker caused by changes in the imaging geometry can be removed or at least reduced.

It will be understood than the above described steps are to be repeated once a new specification for a further change of the imaging geometry is received. In other words, the above described steps are repeated by this time for new input image I2 instead of the earlier image I1. The proposed method and system is envisaged to produce a quasi-continuous stream of filler frames in response to and in concert with quasi-continuous changes in the imaging geometry caused by quasi-continuous movements of one or more of the imager MI's geometry elements.

The following is non-liming numerical to illustrate the method proposed where a plurality of filler frames are computed by sub-dividing the transformation into parts. Real-time coordinates of the imaging equipment IM as per the received specification are converted to image pixel displacements $\Delta \vec{x}(t) = \vec{x}(t) - \vec{x}(t_1)$ where $\vec{x}(t)$ is the known position at a time point $t_1$ later than $t_1$ (as which the image I1 was acquired) and x(t1) is the known position at the instant of the image I1. An implementation of the proposed algorithm involves the following steps:

The first original image I1 acquired at t1 is displayed at $t_1$.

I1 is translated by $\Delta \vec{x}(t1+1\cdot \Delta t/5)$. The result is displayed at $t_1 + 1*\Delta t/5$.

I1 is translated by $\Delta \vec{x}(t1+2\cdot \Delta t/5)$. The result is displayed at $t_1 + 2*\Delta t/5$.

I1 is translated by $\Delta \vec{x}(t1+3\cdot \Delta t/5)$. The result is displayed at $t_1 + 3*\Delta t/5$.

I1 is translated by $\Delta \vec{x}(t1+4\cdot \Delta t/5)$. The result is displayed at $t_1 + 4*\Delta t/5$.

I2 is displayed at $t_2$, with t2 the time at which the next X-ray image I2 is acquired.

The optimal display rate for this is generally the screen refresh rate (typically 60 Hz), and the temporal up-sampling factor is chosen accordingly as explained earlier above. In the numerical example, the transforming of image I1 to obtain the filler images at steps 2-5 is interlaced with the displaying step. Alternatively, some or all of the filler images are computed first, and the display steps are then performed after some or all of the transformation steps have been completed.

The proposed image processing component and method can be used as an add-on for existing imagers by installing for instance suitable motion encoders to pick-up the imaging geometry change specifications.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit (such as the workstation), which might also be part of an embodiment of the present invention. This computing unit may be adapted to perform or induce a performing of the steps of the method described above. Moreover, the computing unit may be adapted to control or operate components of the above-described module. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing module configured to reduce or eliminate image flicker at low frame rates, comprising:
a memory configured to store processor executable instructions;
at least one processor configured to execute the processor executable instructions in order for the image processing module to:
receive i) a first input image acquired of an object by an imaging apparatus at a first geometrical configuration of the imaging apparatus, and ii) a specification of a change from the first geometrical configuration to a second geometrical configuration of the imaging apparatus;
compute, based on the specification, a new image of the object by extrapolating from the first input image; and
display a sequential visualization of the first input image, of the new image, and of the second image acquired at the second geometrical configuration.

2. The image processing module according to claim 1, wherein the specification is supplied as hardware measurement data in relation to the imaging apparatus.

3. The image processing module according to claim 1, wherein the at least one processor is further configured to compute a plurality of new images, one for each of a plurality of received specifications of changes in geometrical configuration of the imaging apparatus, the number of the plurality of new images being dependent on a refresh rate.

4. The image processing module according to claim 1, wherein the imaging apparatus is an X-ray imaging apparatus, and wherein the geometrical configuration of the X-ray imaging apparatus includes at least one of: (i) a position and/or orientation of a support for supporting the object to be imaged during an image acquisition; (ii) a position and/or orientation of an X-ray source of the X-ray imaging apparatus; (iii) a position and/or orientation of a detector of the X-ray imaging apparatus, and (iv) a position and/or orientation of a collimator.

5. The image processing module according to claim 1, wherein the new image comprises image information retained from the first input image and placeholder data that replaces image information from the first input image lost due to the extrapolating.

6. The image processing module according to claim 1, wherein the extrapolating includes moving, relative to a reference coordinate system, the first input image by an amount that corresponds to the change.

7. The image processing module according to claim 1, wherein the imaging apparatus is a fluoroscopic X-ray imaging apparatus.

8. A method for image processing to reduce or eliminate image flicker at low frame rates, comprising:
receiving a first input image acquired of an object by an imaging apparatus at a first geometrical configuration of the imaging apparatus;
receiving a specification of a change from the first geometrical configuration to a second geometrical configuration of the imaging apparatus;
based on the specification, computing a new image by extrapolating from the first input image;
receiving a second image acquired at the second geometrical configuration of the imaging apparatus; and
displaying sequentially the first input image, the new image, and the second image.

9. A non-transitory computer-readable medium having one or more executable instructions stored thereon, which when executed by a processor, cause the processor to perform a method for image processing to reduce or eliminate image flicker at low frame rates, the method comprising:
 receiving a first input image acquired of an object by an imaging apparatus at a first geometrical configuration of the imaging apparatus;
 receiving a specification of a change from the first geometrical configuration to a second geometrical configuration of the imaging apparatus;
 based on the specification, computing a new image by extrapolating from the first input image;
 receiving a second image acquired at the second geometrical configuration of the imaging apparatus; and
 displaying sequentially the first input image, the new image, and the second image.

* * * * *